United States Patent

Semmlow

(10) Patent No.: US 9,226,726 B1
(45) Date of Patent: Jan. 5, 2016

(54) METHOD AND SYSTEM FOR DETECTION OF CARDIAC SOUNDS

(71) Applicant: John L Semmlow, New Brunswick, NJ (US)

(72) Inventor: John L Semmlow, New Brunswick, NJ (US)

(*) Notice: Subject to any disclaimer, the term of this patent is extended or adjusted under 35 U.S.C. 154(b) by 0 days.

(21) Appl. No.: 14/552,842

(22) Filed: Nov. 25, 2014

(51) Int. Cl.
 *A61B 7/04* (2006.01)
 *A61B 5/00* (2006.01)

(52) U.S. Cl.
 CPC ............... *A61B 7/04* (2013.01); *A61B 5/6823* (2013.01); *A61B 5/7221* (2013.01)

(58) Field of Classification Search
 CPC ....... A61B 7/04; A61B 5/7221; A61B 5/7246
 USPC .......................................... 600/528
 See application file for complete search history.

(56) References Cited

U.S. PATENT DOCUMENTS

| | | |
|---|---|---|
| 5,036,857 A | 8/1991 | Semmlow et al. |
| 5,109,863 A | 5/1992 | Semmlow et al. |
| 5,595,188 A | 1/1997 | Kassal |
| 5,807,268 A | 9/1998 | Reeves et al. |
| 5,827,198 A | 10/1998 | Kassal |
| 5,885,222 A | 3/1999 | Kassal |
| 5,913,829 A | 6/1999 | Reeves et al. |
| 6,152,879 A | 11/2000 | Mohler |
| 6,261,237 B1 | 7/2001 | Swanson et al. |
| 6,278,890 B1 | 8/2001 | Chassaing et al. |
| 6,478,744 B2 | 11/2002 | Mohler |
| 6,478,746 B2 | 5/2006 | Sleva et al. |
| 7,520,860 B2 | 4/2009 | Guion-Johnson et al. |
| 7,998,091 B2 | 8/2011 | Carim et al. |
| 8,024,974 B2 | 9/2011 | Bharti et al. |
| 8,333,718 B2 | 12/2012 | Carim et al. |
| 8,715,206 B2 | 5/2014 | Telfort et al. |
| 8,755,535 B2 | 6/2014 | Telfort et al. |
| 2013/0102908 A1* | 4/2013 | Ser et al. .................. 600/484 |

OTHER PUBLICATIONS

Wang, P., Tie, B., Welkowitz, W., Semmlow, J., and Kostis, J. "Modeling Sound Generation in Stenosed Coronary Arteries" Biomedical Engineering, vol. 35, No. 3, pp. 367-374, Mar. 2007.
Semmlow J.L., Welkowitz W., Kostis J., and MacKenzie J.W., "Coronary artery disease-correlates between diastolic auditory characteristic and coronary artery stenosis," IEEE Trans. Biomed. Eng., vol. BME-30, pp. 136-139, 1983.
Semmlow, J., and Rahalkar, K., "Acoustic detection of coronary artery disease," Annual Rev of Biomed, Engr. vol. 9: pp. 449-469, Apr. 2007.
Padmanahban, V., and Semmlow J., Accelerometer type cardiac transducer for detection of low-level heart sounds. IEEE Trans. Biomed Engr. vol. BME-40, pp. 21-28,1993.
Akay, Y.M., Akay, M.A., Welkowitz, W., Semmlow, J.L., and Kostis, J.B., "Noninvasive detection of coronary artery disease: A comparative study of signal processing methods," IEEE Trans. Biomed. Engr. vol. 40, pp. 571-578, 1993.

* cited by examiner

*Primary Examiner* — Paula J Stice
(74) *Attorney, Agent, or Firm* — Marc D. Lowy (57) ABSTRACT

The present invention is a method and system for detection of high-frequency heart sounds for diagnosing heart diseases. One embodiment utilizes an accelerometer-based detector that presents a light load to the chest, is sensitive to the desired high frequency range, and provides a quantitative measurement of the quality of the acquired signal. Two thin piezoelectric flexible sensors, supported by a lightweight mechanical structure, are center-loaded so that they respond to the same mechanical energy and will produce identical electrical signals in the absence of noise. A signal processing system compares the signals from the two sensors to produce an estimate of the signal-to-noise ratio. The two signals can be combined to further improve the signal-to-noise ratio. The invention is designed to be light weight, to have a sensitive sensor mechanism, to provide an estimate of the signal-to-noise ratio of the detected signal, and to be relatively immune to noise.

18 Claims, 6 Drawing Sheets

METHOD AND SYSTEM FOR DETECTION OF CARDIAC SOUNDS

CROSS REFERENCE TO RELATED APPLICATION(S)

Not Applicable.

FIELD OF INVENTION

The present invention relates to a method and system for detection of high-frequency heart sounds for diagnosing heart diseases, and more particularly, a noninvasive method and system which affords reliable diagnostic information in the early stages of coronary artery disease.

BACKGROUND

There are devices presently available to detect acoustic signals from the chest each having its own advantages and disadvantages as described in the review by Semmlow and Rahalkar. The motivation for most of these devices is the detection of sound signatures associated with coronary artery disease as originally described by Semmlow el al. in 1983. Coronary artery disease results from occlusions or blockages of the coronary arteries which supply blood to the heart. Such blockages will produce turbulent blood flow including an auditory correlate. Theoretical studies by Wang et al indicate that said auditory correlates will be at relatively high frequencies: above 200 Hz and as high as 1 kHz. Such sounds are generally too faint and at too high a frequency to be heard through a traditional stethoscope, although murmurs associated with coronary artery disease have occasionally been reported. Acoustic detection of the sounds produced by blood flowing through partially occluded coronary arteries would thereby enable the noninvasive detection of this major disease.

Devices for the detection of cardiac sounds from the chest fall into two broad categories: those that reference the acoustic energy to fixed positions on the chest and those that use an inertial reference; i.e., accelerometers. Most of the existing devices to measure sounds from the chest are chest-referenced such as described in U.S. Pat. Nos. 6,152,879, 6,261,237, and 7,520,860. Some chest-reference microphones have been constructed in arrays of multiple microphones as described in U.S. Pat. Nos. 6,278,890 and 7,037,268. It is also possible to combine multiple sensors to improve the signal level as described in U.S. Pat. No. 8,715,206. Chest-referenced devices require a mechanical means for stabilizing the sensor on the chest which places a relatively heavy mechanical load on the chest. Modified chest-referenced microphones have been constructed using flexible piezoelectric sensors which are attached directly to the chest using some type of temporary adhesive as described in U.S. Pat. Nos. 5,807,268, 5,595,188, 5,827,198, 5,885,222 and 5,913,829. In this approach, differential movements of the chest under the flexible piezoelectric sensor act as a self-reference.

All such chest-referenced devices must of necessity place a moderate-to-heavy load on the chest. Moreover, traditional microphone designs are sensitive to ambient noise from the environment. Flexible adhesive sensors are less sensitive to ambient noise and induce the lightest load, but they do not detect compression waves and are less sensitive to shear waves. Moreover, in addition to the weight of these sensors, there is still considerable mechanical loading as the chest must force flexion in these sensors in order to detect the bioacoustic energy. Mechanical loading decreases the sensitivity of the detection apparatus particularly to high-frequency acoustic signals as documented by Vermarien and Vollenhoven. To improve the sensitivity of chest referenced microphones, efforts to match the acoustic impedance of the microphone to the chest have been attempted as described in U.S. Pat. Nos. 6,152,879 and 6,278,890. While such impedance matching techniques may improve the power transferred to the microphone, they actually reduce signal level and still place a load on the chest.

Studies using chest reference microphones have not shown the ability to consistently detect the acoustic signatures associated with coronary artery disease as summarized in Semmlow and Rahalkar. An accelerometer-based sensor described by Padmanahban et al. and in U.S. Pat. Nos. 5,036,857 and 5,109,863 has produced signals that were moderately successful in detecting coronary artery disease as shown by Akay et al. Other accelerometer-based sensors have been described in U.S. Pat. Nos. 7,998,091, 8,024,974, and 8,333,718. Although these detectors will present a reduced mechanical load on the chest compared to chest-referenced devices, they are still comparatively heavy. Even moderate loads of 10-15 gm produced by these devices will reduce their ability to detect the acoustic signature of coronary artery disease.

Since mechanical loading the chest will reduce the bioacoustic signal, particularly at high frequencies, there is a clear need for an acoustic detector which presents a very light mechanical load to the chest. Specifically, the detector should be less than 10 gm so as to be sensitive to the relatively high frequency signals in the range of 200 to 1200 Hz. Said detector should also be relatively immune to ambient or environmental noise.

The quality of the signal produced by any cardiac microphone will also depend on microphone position and attachment to the chest along with patient factors such as body weight. Hence the quality of signals produced by any detector will vary from patient-to-patient and even measurement-to-measurement. The signals produced by all cardiac microphones developed thus far provide no feedback on the quality of the detected signal. There is therefore a clear need for a detector which provides quantitative information on the quality of the acquired signal over the range of desired frequencies. The present invention accomplishes these objectives.

SUMMARY

The present invention is a method and system for detection of high-frequency heart sounds for diagnosing coronary artery disease. One embodiment of this invention utilizes an accelerometer-based detector that presents a very light load to the chest, is sensitive to the desired high frequency range, and provides a quantitative measurement of the quality of the acquired signal.

It is therefore a primary objective of the invention to be very light in weight so as to present a minimum mechanical load to the chest. It is another objective of the invention to have a sensor mechanism that is very sensitive to mechanical energy in the desired frequency range of 200 to 1200 Hz and minimizes electrical interference. Another objective of the invention to provide information on signal quality as a measurement of the signal-to-noise ratio of the detected signal where signal is defined as acoustic energy from the chest and noise is electrical noise from the transducer, electronics, or electrical interference from the environment. It is yet another aspect of this invention to be relatively immune to ambient or environmental acoustic noise by having an accelerometer-type design that is inherently immune to such artifacts.

In view of these objectives, one embodiment of this invention comprises two thin piezoelectric elements that are sensitive to bending moments. In another aspect of the invention, these elements are supported at each end by a lightweight mechanical structure and the two bending moment sensors are center-loaded by the same low-mass weight so that they respond to the same mechanical energy and will produce identical signals in the absence of noise. In another aspect of this invention, each of the two sensor elements produces a bipolar signal with is differentially combined in the sensor electronics to reduce electrical interference.

According to yet another aspect of the invention, the signals produced by the two identically loaded bending moment sensors are compared using a unique correlation analysis. Signal processing means are provided that compensate for unequal time shifts in the two signal channels, perform the correlation analysis, and convert the correlation value between the two signals to a signal-to-noise ratio (SNR) that can be given in decibels (dB). In another aspect of this invention, the signals are first band-limited to narrow frequency ranges before the correlation analysis so that said analysis provides the SNR as a function of frequency.

Other features and advantages of the present invention will become apparent from the following more detailed description, taken in conjunction with the accompanying drawings, which illustrate, by way of example, the principles of the invention.

BRIEF DESCRIPTION OF THE DRAWING(S)

The foregoing Summary as well as the following detailed description will be readily understood in conjunction with the appended drawings which illustrate embodiments of the invention. In the drawings.

DETAILED DESCRIPTION OF ILLUSTRATIVE EMBODIMENT(S)

The present invention is a method and system for detection of high-frequency heart sounds for diagnosing coronary artery disease. One embodiment of this invention comprises an accelerometer-based detector 1 that converts bio-acoustic information to electrical signals while presenting a very light load to the chest and providing sensitivity to the desired high frequency range. The benefits produced by the invention include, in various embodiments, quantitative measurements of the quality of electrical signals acquired from a patient's cardiac bio-acoustic information.

Figure 1:
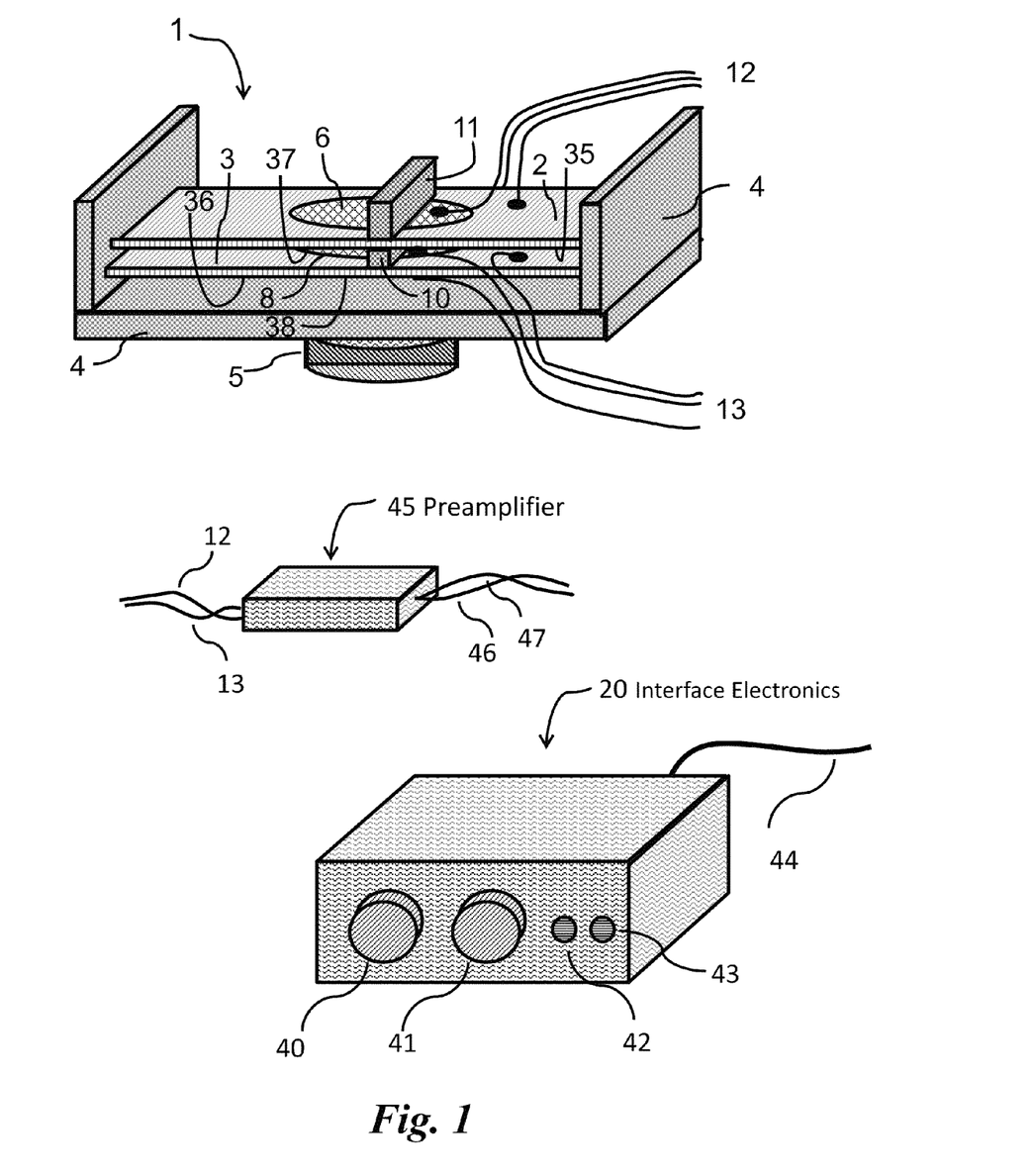
FIG. 1 is a perspective view illustrating one embodiment of a cardiac sound detector and associated electronics.

FIG. 1 illustrates one embodiment of the invention comprising an accelerometer detector 1, preamplifier unit 45, and interface electronics unit 20. The accelerometer detector 1 comprises, in some embodiments, an accelerometer type transducer-sensor that converts bio-acoustic information produced by a human heart to two electrical signals representing the same bio-acoustic information. In some embodiments, the accelerometer detector 1 may comprise single, dual, or multiple sensors. In the accelerometer detector 1, two low-mass, substantially planar, flexible sensors 2, 3 are attached at their edges to a lightweight frame 4. The frame 4 is constructed using a strong but light material such as titanium, plastic, or even balsa wood. The frame 4 is mechanically connected to the patient's chest through base plate 5. Firm attachment to the patient's chest is assured through the use of a viscous gel, double-sided tape, or other temporary adhesive. In other embodiments, other sensor types including fixed reference sensors could be used.

In one embodiment, each flexible sensor 2,3 contains piezoelectric material on the upper surfaces 6,8 of each flexible sensor 2,3. The lower surfaces 35,36 of each flexible sensor 2,3 also contain piezoelectric material, 37,38. When each flexible sensor 2,3 bends, the piezoelectric material on one surface is in tension while the piezoelectric material on the opposite surface is in compression. In an alternative embodiment (not shown), four flexible sensors with piezoelectric material on only one side could be used with two flexible sensors placed upward and two flexible sensors placed downward. In other embodiments, the flexible sensors could be constructed from piezoelectric film (e.g., PVDF2 film), piezo-resistive material, or stain gages.

The two flexible sensors 2,3 are coupled at the center by a beam 10, so both flexible sensors 2,3 are subject to the same bending action. Both flexible sensors 2,3 are center-loaded by a low-mass weight 11, such that the bending elements 2,3 respond similarly to accelerations produced by vibrations of the user's chest. Center loading provides a more compact configuration, but in an alternative embodiment each flexible sensor 2,3 could be loaded with end weights and supported at the center. In accordance with one of the embodiments of the invention, the thickness of the two flexible sensors 2,3 is adjusted to produce resonant frequencies of approximately 1000 Hz, so as to maximize the signal produced at the higher frequencies.

The preamplifier unit 45 receives the two differential sensor outputs 12,13 from each flexible sensor 2, 3 and adds them differentially so that each flexible sensor 2,3 produces an electric signal that is a separate version of the bioacoustic information. In the absence of electronic noise, the two electrical output signals 46,47 should be identical.

The interface electronics unit 20 amplifies and filters the two signals 46,47 from the preamplifier unit 45. In this embodiment, the amplitudes of the signals 46,47 are adjusted manually using controls 40,41. In an alternate embodiment, signal amplitude could be adjusted by the computing unit 19 (FIG. 2), based on a desired signal amplitude range as described below. The interface electronics includes input connectors 42,43 for the two signals 46,47 from the preamplifier unit 45. The interface electronics unit 20 also contains an analog-to-digital converter 17 (FIG. 2) which converts the analog signals from the filters 16 to digital signals 48,49 for use by the computing unit 19.

Figure 2:
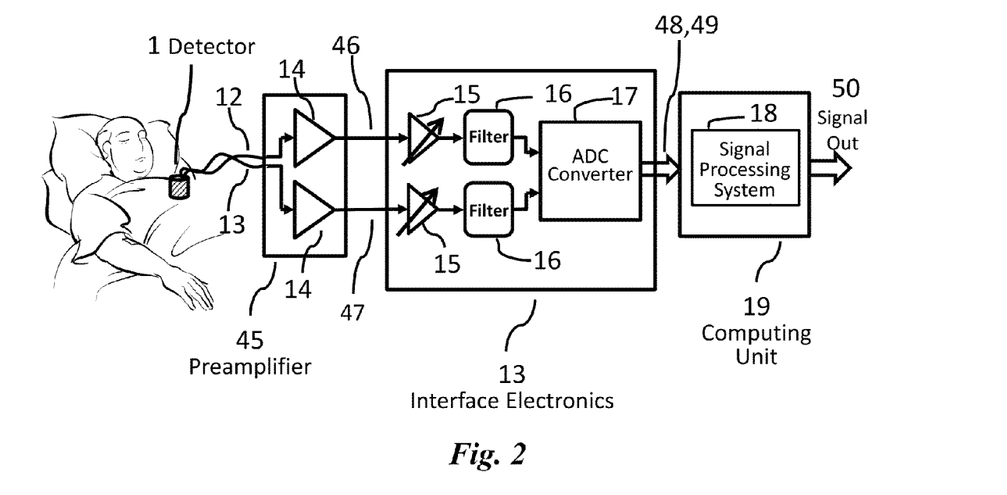
FIG. 2 is a schematic of the overall system illustrating one embodiment of system electronics and external computing device, including signal processing means.

In FIG. 2 is illustrated a schematic of the overall system including the accelerometer detector 1, preamplifier unit 45, interface electronics unit 20, and computing unit 19 containing a signal processing system 18.

The preamplifier unit 45, takes the differential output signals 12,13 from the detector 1, combines them, and amplifies the resultant signal. In the preferred embodiment the preamplifier unit 45 is located in a separate electronics assembly proximate to the detector 1. In an alternative embodiment, the preamplifier unit 45 could be mounted inside the detector 1. In another embodiment the preamplifier unit 45 could serve as the mass-loading weight 11 of the detector 1, so that no additional weight need be added to the detector 1. The preamplifier unit 45 is constructed from standard low-noise instrumentation amplifiers 14 well-known in the art.

The interface electronics unit 13, receives the two signals 46,47 from the output of the preamplifier unit 45. Each signal is first sent to variable gain amplifiers 15, which adjust the signal to a desired amplitude using controls 40,41. The amplitude is normally adjusted so that the loud valve sounds take up the full range available to the digital signal. In one embodiment, the amplitude of these signals is adjusted manually by the operator by observing the two signals on the screen of the computing unit 19. In an alternate embodiment, signal amplitude could be adjusted by the computing unit 19, based on a desired signal amplitude range. The two signals are then sent to anti-aliasing filters 16. In one embodiment, these filters 16 are bandpass Butterworth filters that attenuate frequencies less than 150 Hz and greater than 1500 Hz. In alternative embodiments, other filter types and frequencies ranges could be used. In the final stage of the interface electronics 13, the two filtered signals are sent to a standard analog-to-digital converter (ADC) 17, preferably having a 16-bit or better conversion accuracy. The ADC 17 generates two digital signals 48,49 and sends them to the computing unit 19 through a USB port or other input on the computing unit 19.

In one embodiment of the invention, a standard laptop computer could be used for the computing unit 19. The computing unit 19 receives the digitized signal from the ADC 17, stores the signals 48,49 temporarily or permanently, and implements the signal processing system 18. However, in alternative embodiments, a specially designed computer (not shown) using a dedicated microprocessor could be used to perform these operations. In still another embodiment, a tablet computer (not shown) or even a mobile telephone (not shown) could be used to implement the signal processing system 18.

Figure 3:
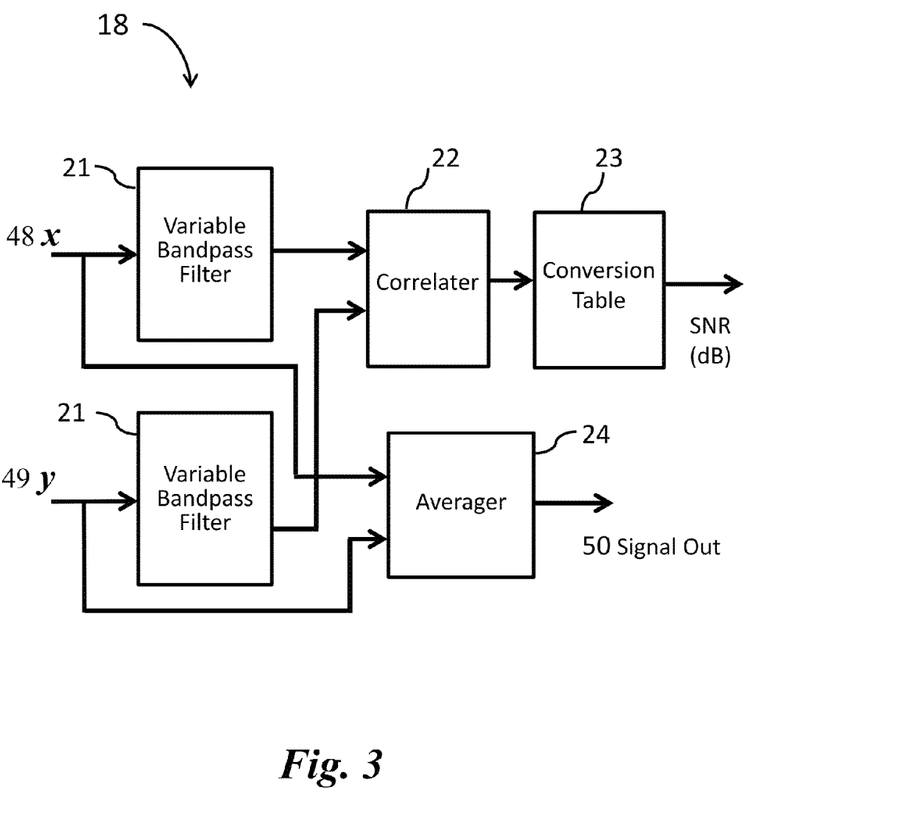
FIG. 3 is a block diagram illustrating one embodiment of the signal processing system 18.

In FIG. 3 is illustrated a block diagram of one embodiment of the signal processing system 18 (FIG. 2), which consists of variable bandpass filters 21, a correlater 22, a conversion table, 23, and a signal averager 24. The correlator 22, performs a standard Pearson correlation between the two signals as described by the equation:

$$r_{xy} = \left(\frac{1}{(N-1)\sigma_y\sigma_x}\right)\sum_{n=1}^{N}(x[n] - x_{avg} + k)(y[n] - y_{avg}) \quad \text{Equation 1}$$

where x and y are the two signals, σx and σy are the standard deviations of signal x and y respectively, n is the data index and N is the number of points in the signal array. The integer, k, can be positive or negative and is used to compensate for any unequal time shifts in the two signals produced by the electronic means, 13. In one embodiment, the value of k is determined using cross-correlation and is set to the value that produces the highest correlation, $r_{xy}$.

The signal processing system 18 also includes an averager 24 (FIG. 3), which combines the two input signals algebraically to produce a single signal 50 with improved SNR. This signal would then be used by subsequent additional software in a system for the identification of auditory correlates of coronary artery disease.

The signal processing system 18 also includes variable bandpass filters 21, so that the SNR can be determined at different frequencies. In some embodiments, narrow band filters having bandwidths of 100 Hz and center frequencies spaced at 25 Hz intervals over a frequency range of 150 to 900 Hz are used, but other bandwidths, center frequencies and frequency ranges are possible. Said filters are 4th-order Butterworth bandpass filters implemented by applying the Butterworth filter coefficients in a recursive and non-recursive manner as given by the equation:

$$y[n] = \sum_{k=0}^{K} b[n]x[n-k] - \sum_{l=1}^{L} a[n]x[n-l] \quad \text{Equation 2}$$

where n is the data index, b[k] and a[l] are the Butterworth non-recursive and recursive filter coefficients, respectively. These coefficients are adjusted to give the desired filter cutoff frequencies. For a 4th-order Butterworth filter, K=L=9. Other embodiments of the invention could employ different bandpass filters and achieve similar results.

Figure 4:
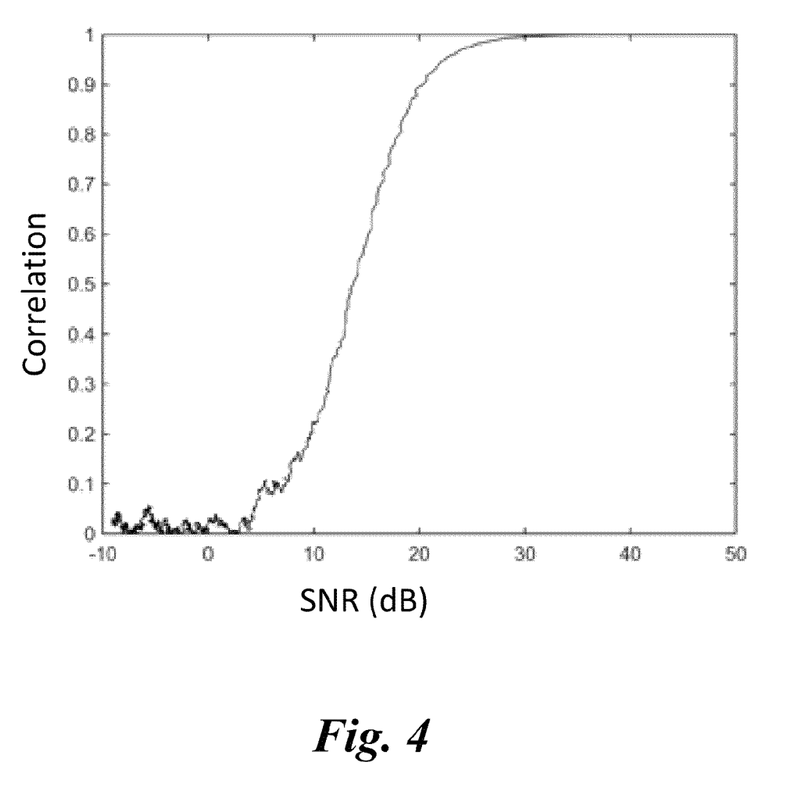
FIG. 4 is a graph illustrating the relationship between the correlation of two signals and the corresponding signal-to-noise ratio.

FIG. 4 illustrates a graph showing the relationship between the correlation of the two signals and the corresponding signal-to-noise ratio (SNR). The Pearson correlation is converted to dB using a conversion table algorithm 23 (FIG. 3). This table was developed empirically through simulation, by determining the correlation between two initially identical signals after varying amounts of noise is added to the two signals. The relationship so determined, and embedded in the conversion table 23, is shown in FIG. 4. Note that when the SNR of each signal equals 0.0 dB (indicating equal signal and noise), the Pearson correlation is 0.5. In another embodiment of the invention, alternative correlation normalizations could be used in conjunction with a modified correlation-to-SNR conversion table 23.

Figure 5:
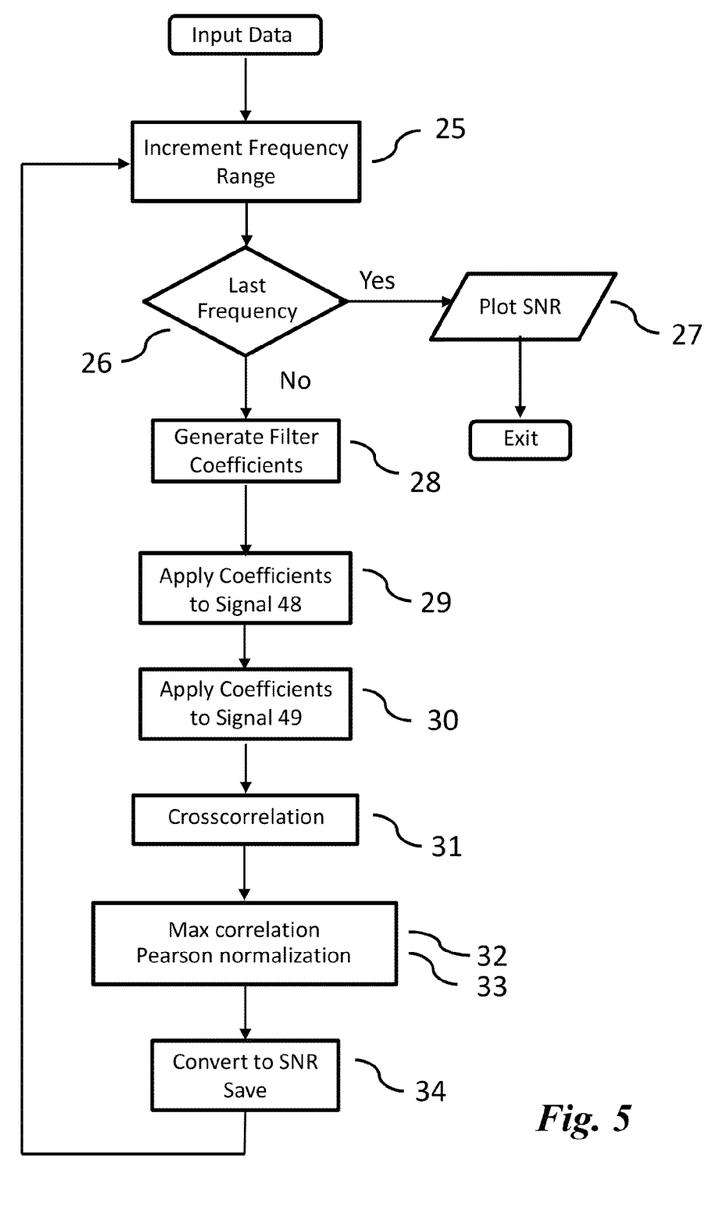
FIG. 5 is a flow diagram illustrating the signal processing system.

FIG. 5 illustrates a flow diagram of the signal processing system. In step 25, the frequency range is selected from a table of desired frequency ranges, and the software tests to see if the last desired frequency range has been analyzed (step 26). If the last desired frequency range has been analyzed, processing continues at step 27, which displays the signal-to-noise ratio as a function of frequency. The program then exits.

In step 26, if the last desired frequency range has not been analyzed, processing continues at step 28 by first determining the Butterworth filter coefficients, 28. In step 29 the coefficients are applied to signal 48 (FIG. 3), and in step 30 the coefficients are applied to signal 49 (FIG. 3), in accordance with Equation 2. The two filtered signals are cross-correlated in step 31, in accordance with Equation 1. In step 32 the maximum correlation is determined, and is normalized to the Pearson correlation in step 33, by dividing by Nσxσy, again in accordance with Equation 1. A lookup table defining the function shown in FIG. 4 is used to convert the Pearson correlation to a SNR in step 34. The SNR values are determined for each frequency range and saved. The loop then continues at step 25.

Figure 6:
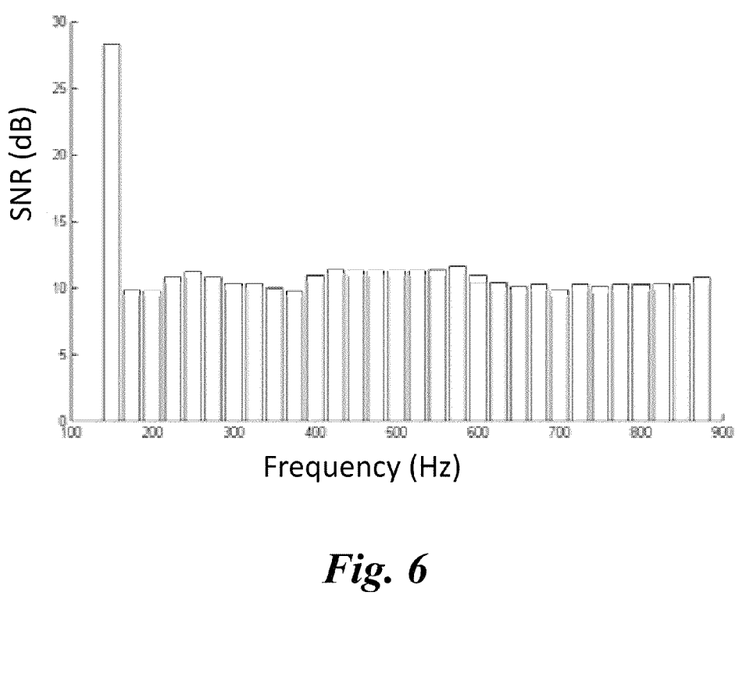
FIG. 6 is a graph illustrating the signal-to-noise ratio as a function of frequency obtained from the system applied to a typical subject.

FIG. 6 illustrates a graph showing the signal-to-noise ratio as a function of frequency obtained from the system applied to a typical subject. Note that in this patient, the cardiac detector, 1, produces a positive SNR for all frequencies up to 900 Hz.

The invention is typically operated by medical personnel who are performing various types of cardiac testing involving sounds produced by the heart. During operation of the invention, the user is provided, either by a display unit or by other methods, the signal-to-noise ratio for the cardiac bio-acoustic signals received from the accelerometer detector attached to the patient's chest. By obtaining an accurate measurement of the signal-to-noise ratio, the invention user may thus determine if the quality of the bio-acoustic cardiac signals meets the requirements for the medical test being conducted.

While embodiments of the invention have been described in detail above, the invention is not limited to the specific embodiments described above, which should be considered as merely exemplary illustrations set forth for a clear understanding of the principles of the invention. Further variations, modifications, extensions, or equivalents of the invention may be developed without departing from the scope of the invention. It is therefore intended that the invention not be limited to the particular embodiments disclosed as the best mode contemplated for carrying out this invention, but that the invention will include all the embodiments falling within the scope of the appended claims.

What is claimed is:

1. A computer implemented system for determining cardiac acoustic signal quality, the system comprising:
   a cardiac acoustic signal detector connected to an amplifier;
   an analog-to-digital converter connected to said amplifier;
   a computing device connected to said analog to digital converter; and
   computer executable instructions operative on said computing device configured to:
   perform a correlation function to calculate a maximum correlation between said cardiac acoustic signals;
   convert said maximum correlation to a signal-to-noise ratio for said cardiac acoustic signals;
   delivering a quantitative measurement of said signal-to-noise ratio to an output device; wherein the output device includes a user interface for visual representation of the quality of said cardiac acoustic signals; wherein said quality of said cardiac acoustic signal can be accurately verified.

2. The system of claim 1, further comprising normalizing said maximum correlation using a Pearson normalization.

3. The system of claim 1, wherein converting said maximum correlation comprises using a lookup table to convert said maximum correlation to said signal-to-noise ratio.

4. The system of claim 1, wherein said signal-to-noise ratio is measured in decibels.

5. The system of claim 1, further comprising initially band-limiting said cardiac acoustic signals using a filter bank tuned to appropriate frequencies such that the signal-to-noise ratio is determined as a function of signal frequency.

6. The system of claim 5 further comprising displaying graphically at a user interface said signal-to-noise ratio as a function of frequency.

7. The system of claim 1, wherein determining said maximum correlation comprises applying a cross-correlation function to said cardiac acoustic signals.

8. The system of claim 1, further including combining said cardiac acoustic signals to produce an improved signal-to-noise ratio in a resultant combined signal.

9. The system of claim 1, wherein said cardiac acoustic signal detector comprises a cardiac accelerometer detector.

10. A computer implemented method for determining cardiac acoustic signal quality, the method comprising:
    amplifying at least two cardiac acoustic signals received from a cardiac acoustic signal detector;
    performing an analog-to-digital conversion on said cardiac acoustic signals;
    receiving said cardiac acoustic signals at a computing device;
    wherein the computing device performs a correlation function to calculate a maximum correlation between said cardiac acoustic signals;
    convert said maximum correlation to a signal-to-noise ratio for said cardiac acoustic signals;
    deliver a quantitative measurement of said signal-to-noise ratio to an output device; wherein the output device includes a user interface for visual representation of the quality of said cardiac acoustic signals; wherein said quality of said cardiac acoustic signal can be accurately verified.

11. The method of claim 10, further comprising normalizing said maximum correlation using a Pearson normalization.

12. The method of claim 10, wherein converting said maximum correlation comprises using a lookup table to convert said maximum correlation to said signal-to-noise ratio.

13. The method of claim 10, wherein said signal-to-noise ratio is measured in decibels.

14. The method of claim 10, further comprising initially band-limiting said cardiac acoustic signals using a filter bank tuned to appropriate frequencies such that the signal-to-noise ratio is determined as a function of signal frequency.

15. The method of claim 14, further comprising displaying graphically at a user interface said signal-to-noise ratio as a function of signal frequency.

16. The method of claim 10, wherein determining said maximum correlation comprises applying a cross-correlation function to said cardiac acoustic signals.

17. The method of claim 10, further including combining said cardiac acoustic signals to produce an improved signal-to-noise ratio in a resultant combined signal.

18. The method of claim 10, wherein said cardiac acoustic signal detector comprises a cardiac accelerometer detector.

* * * * *